(12) United States Patent
Bogoev et al.

(10) Patent No.: US 8,039,264 B2
(45) Date of Patent: Oct. 18, 2011

(54) COMPOSITIONS, METHODS AND KITS FOR BIARSENICAL FLUOROPHORE LABELING

(75) Inventors: Roumen Bogoev, San Marcos, CA (US);
Joseph Amshey, Ecinitas, CA (US);
George Hanson, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 31 days.

(21) Appl. No.: 12/510,995

(22) Filed: Jul. 28, 2009

(65) Prior Publication Data
US 2011/0014710 A1    Jan. 20, 2011

Related U.S. Application Data

(63) Continuation of application No. 10/971,606, filed on Oct. 22, 2004, now abandoned.

(60) Provisional application No. 60/515,575, filed on Oct. 28, 2003, provisional application No. 60/515,011, filed on Oct. 27, 2003, provisional application No. 60/514,447, filed on Oct. 24, 2003.

(51) Int. Cl.
*G01N 33/68* (2006.01)

(52) U.S. Cl. .............. 436/86; 436/56; 436/73; 436/119; 436/164; 436/172

(58) Field of Classification Search .................... 436/56, 436/73, 86, 119, 164, 172; 422/68.1, 82.05, 422/82.08
See application file for complete search history.

(56) References Cited

U.S. PATENT DOCUMENTS

| 4,478,823 | A | 10/1984 | Sanderson |
| 5,932,474 | A | 8/1999 | Tsien et al. |
| 6,008,378 | A | 12/1999 | Tsien et al. |
| 6,054,271 | A | 4/2000 | Tsien et al. |
| 6,124,255 | A | 9/2000 | Schlag et al. |
| 6,130,101 | A | 10/2000 | Mao et al. |
| 6,451,569 | B1 | 9/2002 | Tsien et al. |
| 6,686,458 | B2 | 2/2004 | Tsien et al. |
| 6,902,936 | B2 | 6/2005 | Qiu et al. |
| 2005/0095615 | A1* | 5/2005 | Welch et al. ............ 435/6 |
| 2005/0136449 | A1 | 6/2005 | Hanson |
| 2005/0176065 | A1 | 8/2005 | Hanson |
| 2006/0110788 | A1 | 5/2006 | Kudlicki |
| 2009/0136983 | A1* | 5/2009 | Hanson ............... 435/29 |

FOREIGN PATENT DOCUMENTS
WO    WO-99/21013    4/1999

OTHER PUBLICATIONS

2005/040197, , "PCT ISR", Jan. 25, 2005.
Adams, Stephen R. et al., "New Biarsenical Ligands and Tetracysteine Motifs for Protein Labeling in Vitro and in Vivo: Synthesis and Biological Applications.", *Journal of the American Chemical Society* vol. 124 2002 , 6063-6076.
Gaietta, Guido et al., "Multicolor and Electron Microscopic Imaging of Connexin Trafficking", *Science* vol. 296, American Association for the Advancement of Science Apr. 19, 2002 , 503-507.

(Continued)

*Primary Examiner* — Maureen Wallenhorst

(57) ABSTRACT

Methods, compositions, and kits for labeling tetracysteine-tagged proteins with biarsenical fluorophores with increased specificity, including compositions, methods and kits particularly adapted for labeling of tetracysteine-tagged proteins to be resolved within an electrophoresis gel.

41 Claims, 9 Drawing Sheets

OTHER PUBLICATIONS

Griffin, B. A. et al., "Fluorescent labeling of Recombinant Proteins in Living Cells with Flash", *Methods in Enzymology* 327 2000, 565-578.

Griffin, B A. et al., "Specific Covalent Labeling of Recominant Protein Molecules Inside Live Cells", *Science* vol. 281 Jul. 10, 1998, 269-272.

Kalef, E. et al., "Arsenical-Based Affinity Chromatography of Vicinal Dithiol-Containing Proteins:Purification of L1210 Leukemia Cytoplasmic Proteins and The Recombinant Rat C-ERB Abeta1 T3 Receptor", *Analytical Biochemistry* vol. 212 1993, 325-334.

U.S. Appl. No. 10/954,951, filed Jun. 23, 2005, Hanson, George.

Stroffekova, Katarina et al., "The protein-labeling reagent FLASH-EDT2 binds not only to CCXXCC motifs but also non-specifically to endogenous cysteine-rich proteins", *Eur J. Physiol* 442 2001, 859-866.

Thorn, Kurt S. et al., "A Novel Method of Affinity-Purfying Proteins Using a Bisarsenical Fluorescein.", *Protein Sci.* 9 2002, 213-217.

U.S. Appl. No. 10/971,606, "Non-Final Office Action mailed on Jan. 28, 2009", 10.

U.S. Appl. No. 10/971,606, "Non-Final Office Action mailed on Jul. 9, 2008", 12.

U.S. Appl. No. 10/971,606, "Response to Non-Final Office Action filed on Nov. 10, 2008", 4.

\* cited by examiner

SimplyBlue DETECTION

LUMIO DETECTION

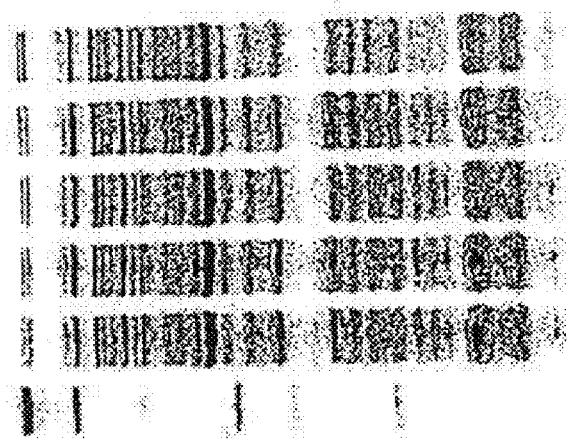
FIG. 6B SimplyBlue DETECTION
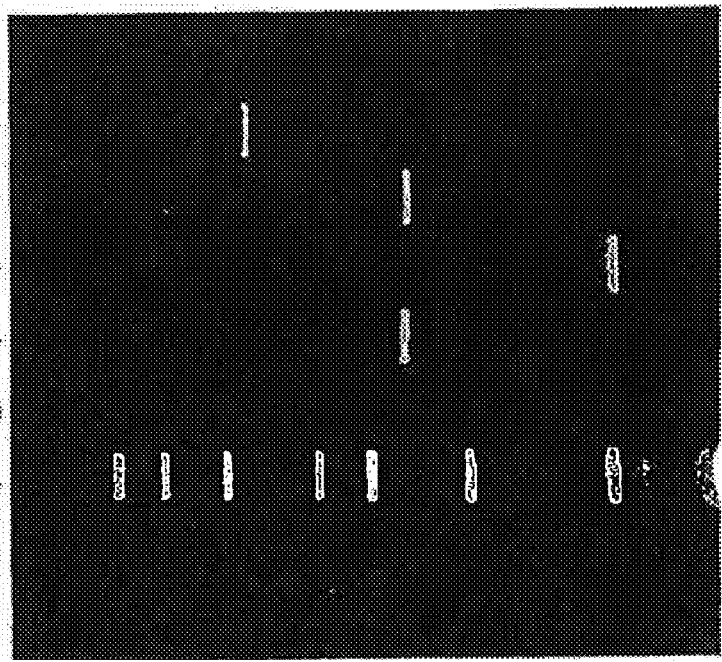
FIG. 6A LUMIO DETECTION

SimplyBlue DETECTION

LUMIO DETECTION

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Variable amino acid

<400> SEQUENCE: 1
```

```
Cys Cys Xaa Xaa Cys Cys
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Cys Pro Gly Cys Cys
  1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Gly Gly Cys Cys Pro Gly Cys Cys Gly Gly Gly
  1               5                   10

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gctggtggct gttgtcctgg ctgttgcggt ggcggc                            36

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

His His His His His His
  1               5
```

COMPOSITIONS, METHODS AND KITS FOR BIARSENICAL FLUOROPHORE LABELING

CROSS-REFERENCE TO RELATED APPLICATIONS

This application is a continuation of U.S. application Ser. No. 10/971,606, filed Oct. 22, 2004, now abandoned, which claims the benefit of U.S. provisional patent applications Ser. No. 60/514,447, filed Oct. 24, 2003; Ser. No. 60/515,011, filed Oct. 27, 2003; and Ser. No. 60/515,575, filed Oct. 28, 2003; the disclosures of all of which are incorporated herein by reference in their entireties.

SEQUENCE LISTING

The instant application contains a Sequence Listing as disclosed in the paper copy of the Sequence Listing for the present application and is incorporated by reference in its entirety.

FIELD OF THE INVENTION

The invention is drawn to compositions, methods and kits for labeling tetracysteine-tagged proteins with biarsenical fluorophores, with increased specificity, including compositions, methods and kits particularly adapted for labeling of tetracysteine-tagged proteins to be resolved within an electrophoresis gel.

BACKGROUND OF THE INVENTION

Recently, a new class of fluorophore derivatives of tremendous value in the detection, visualization, and purification of recombinant proteins has been introduced.

These biarsenical fluorophore derivatives, as adducts with EDT (1,2-ethanedithiol), are self-quenching: the small size of the EDT moieties permits free rotation of the arsenic atoms, which quenches fluorescence of the fluorophore. The essentially nonfluorescent molecule is rendered fluorescent by competitive displacement of the EDT moiety by a specific tetracysteine peptide motif (CCXXCC, (SEQ ID NO: 1) where "X" represents any amino acid), an engineered sequence that is uncommon in natural proteins; binding to the tetracysteine motif constrains motion of the arsenic atoms, unquenching the fluorophore. Griffin et al., Science 281:269 (1998); Griffin et al., Methods Enzymol. 327:565-78 (2000); Adams et al., J. Amer. Chem. Soc. 124:6063-6076 (2002); Gaietta et al., Science 503-507 (2002); U.S. Pat. Nos. 5,932,474, 6,054,271; 6,451,569; 6,008,378; U.S. patent application publication no. 2003/0083373, and international patent application publication no. WO 99/21013, the disclosures of which are incorporated herein by reference in their entireties.

Advantages of the biarsenical fluorophores as fluorescent protein labeling reagents include small size, ability of the $EDT_2$ adducts to cross cell membranes, ability to recognize a binding domain that is sufficiently small as not to interfere substantially with the function of the protein to which it is fused, nanomolar (or lower) dissociation constant for binding to the tetracysteine motif, rapid conversion from a nonfluorescent to a fluorescent state upon binding, and the reversibility of its binding upon addition of a high concentration (millimolar) of EDT.

The biarsenical derivative of fluorescein that is most commonly used is 4'-5'-bis(1,3,2-dithioarsolan-2-yl)fluorescein-(2,2-ethanedithiol)$_2$, known as FlAsH™-$EDT_2$ or Lumio™ Green, and is available commercially (Invitrogen Corp., Carlsbad, Calif.). The red-fluorescing biarsenical resorufin derivative, known as ReAsH™ or Lumio™ Red, is also available commercially; methods of synthesizing other such biarsenical fluorophores, such as CHoXAsH-$EDT_2$ and HoX-AsH-$EDT_2$ are described in the literature.

Tetracysteine biarsenical affinity tags (FlAsH™ tags) have been successfully incorporated at either the N- or C-termini of proteins, as well as exposed surface regions within a protein and have been used to permit visualization of recombinant proteins expressed within living cells, and in SDS-PAGE gels. Griffin et al. 1998, Griffin et al. 2000, Adams et al. 2002, supra.

In PAGE gels, inclusion of the FlAsH-$EDT_2$ reagent in the sample loading buffer allows rapid detection of recombinant proteins in whole cell lysates using a standard UV light box without the need for western blotting or other more laborious protein detection methods.

Although the preferred tetracysteine motif occurs rarely in natural proteins, permitting specific labeling of proteins to which the tetracysteine motif has been recombinantly fused, FlAsH-$EDT_2$ has been shown additionally to bind to endogenous cysteine-containing proteins, Stroffekova et al., Pflugers Arch.-Eur. J. Physiol. 442:859-866 (2001), which increases background fluorescence. Stroffekova et al. suggest that FlAsH™ binding to the vicinal cysteines in the C—X—X—C protein motif of endogenous proteins may limit the use of FlAsH-$EDT_2$ to staining recombinant proteins expressed at a high level in cells with a naturally low background.

Given the advantages of biarsenical fluorophores as labeling and purification reagents for recombinantly tagged proteins, there is a need in the art for compositions, methods, and kits that permit tetracysteine-labeled fusion proteins to be labeled with biarsenical fluorophores with decreased reactivity with endogenous protein motifs. There is a particular need in the art for compositions, methods and kits that provide increased specificity of labeling of tetracysteine-tagged recombinant proteins resolved within electrophoresis gels.

SUMMARY OF THE INVENTION

The present invention solves these and other needs in the art by providing methods, compositions, and kits for detecting, characterizing and/or purifying tetracysteine-tagged proteins with increased specificity.

We have found that we can reduce the spurious binding of biarsenical fluorophores to vicinal cysteines of endogenous proteins by using mono- and details to compete with the binding reaction; with the compositions, methods and kits of the present invention, such competition does not substantially hinder the desired binding of the fluorophore to a tetracysteine tag. The compositions, methods and kits of the present invention are useful in improving specificity of biarsenical fluorophore binding in both protein detection methods and protein purification methods.

We have also found, surprisingly, that the resulting increase in specificity can be lost during electrophoresis: without intending to be bound by theory, it appears that the pH of certain gels precludes migration of the uncharged mono- and di-thiols; comigration of the biarsenical fluor and proteins in the gel thus permits the biarsenical fluorophores to bind to vicinal thiols that had earlier been blocked by the mono- and dithiol reagents. For in-gel staining of tetracysteine-tagged recombinant proteins, the invention thus provides compositions and methods for reductive competition in the presence of the biarsenical fluor, followed by alkylation, effectively capping vicinal thiols and preventing binding of the fluor to vicinal thiols during electrophoresis, leading to a substantial improvement in specificity during in-gel staining reactions.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 6A shows the fluorescent detection of FlAsH-tagged proteins expressed in vitro, with the in vitro reactants treated with the compositions and according to the methods of the present invention and resolved in a 4-12% NuPAGE gel run with MES running buffer; FIG. 6B shows the same gel after staining with a visible dye;

DETAILED DESCRIPTION

Figure 1:
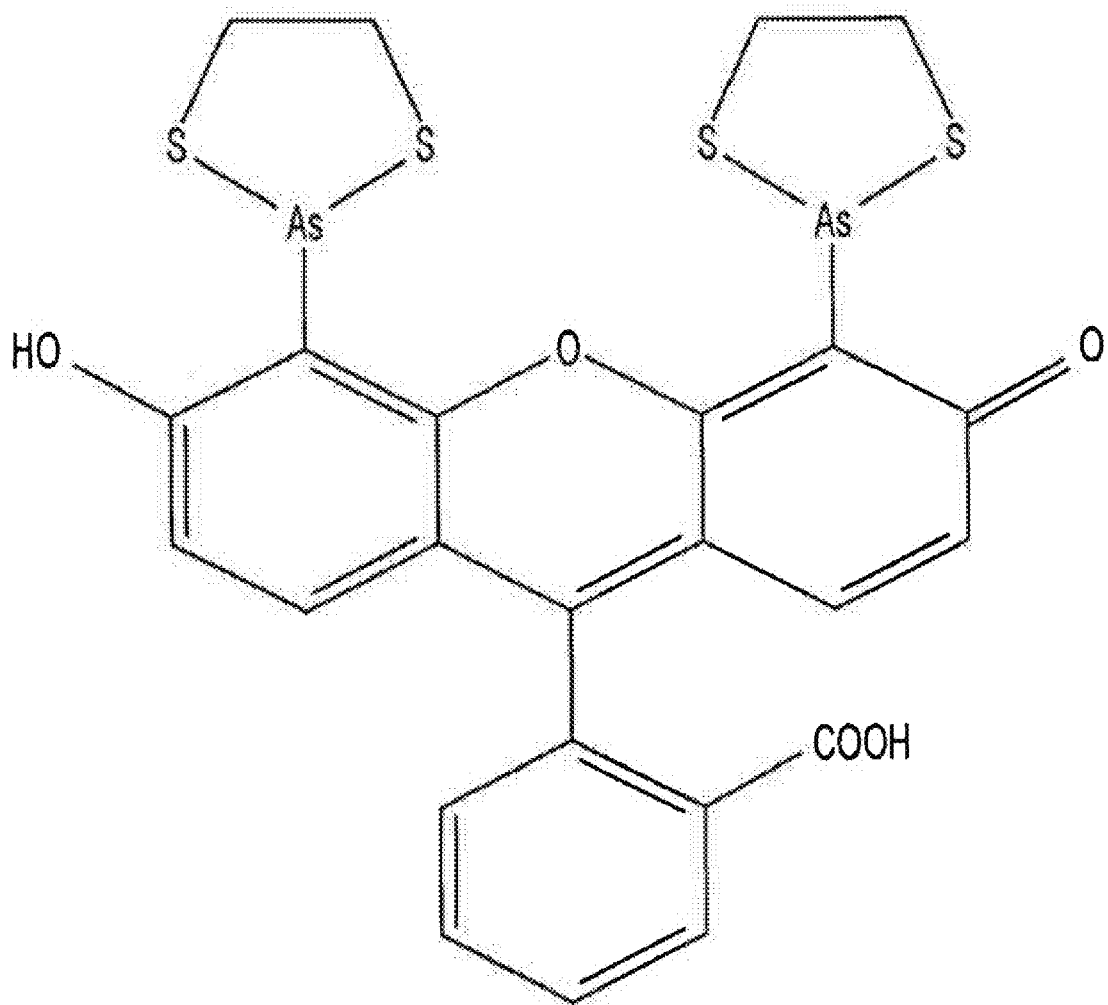
FIG. 1 shows the structure of FlAsH-EDT$_2$, a known biarsenical fluorophore.
Figure 2:
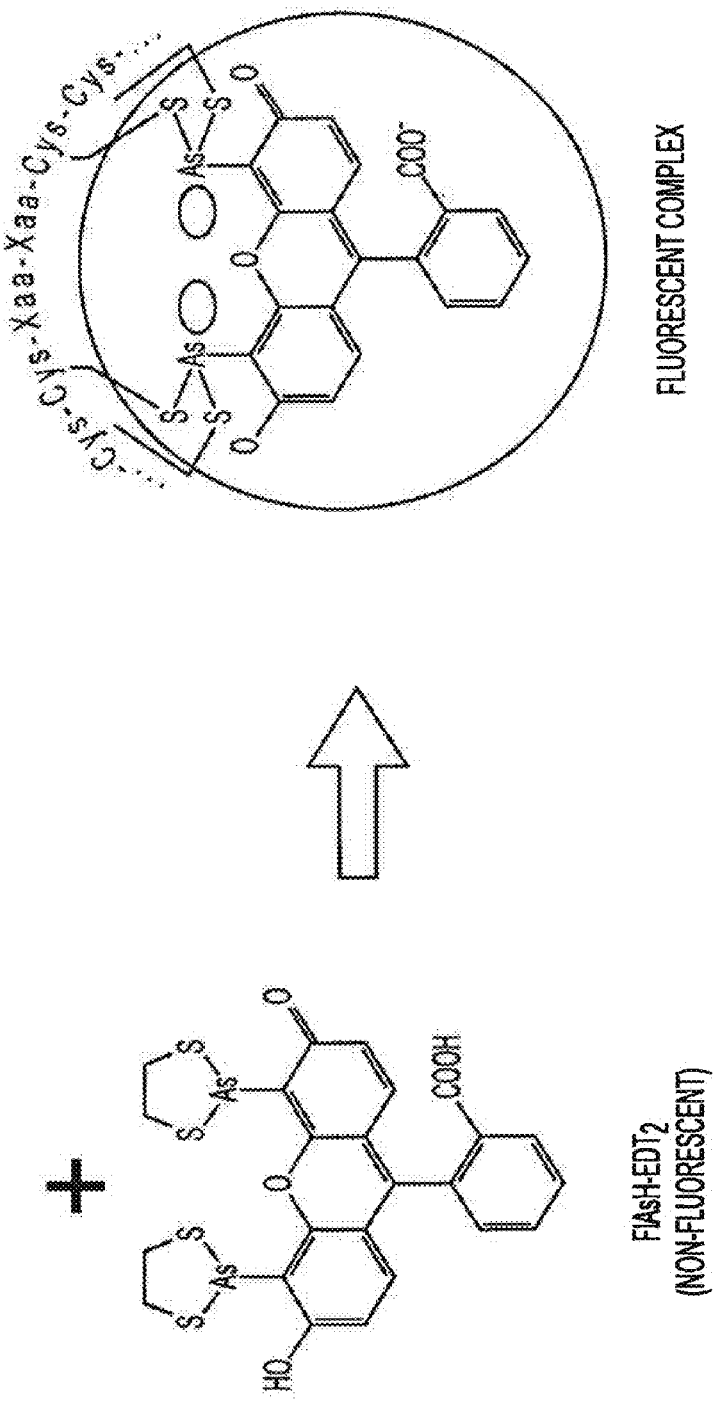
FIG. 2 shows the unquenching of FlAsH™ fluorescence upon competitive displacement of both EDT moieties by the tetracysteine tag of a recombinantly engineered protein (SEQ ID NO: 1), according to the prior art.
Figure 3:
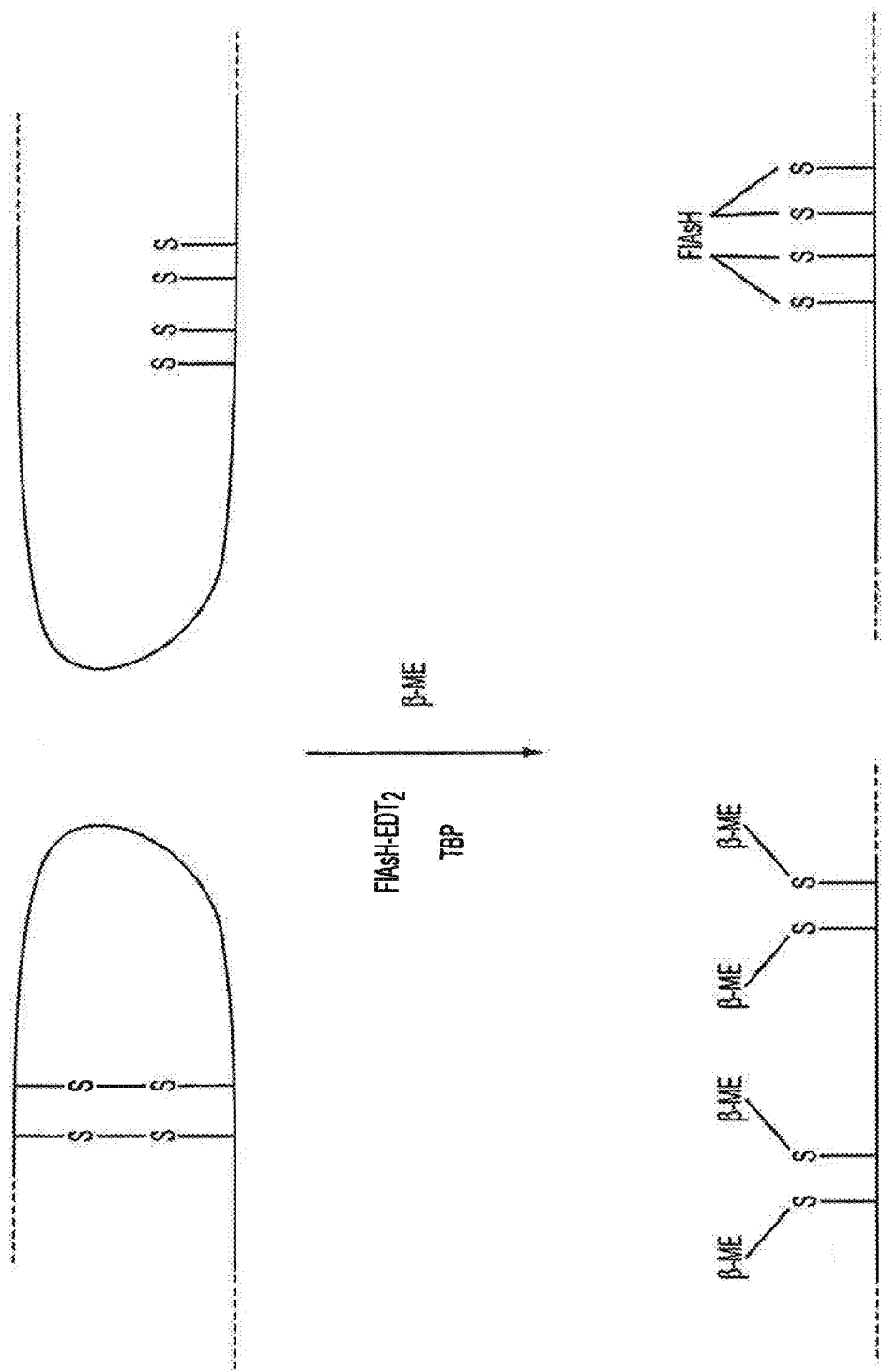
FIG. 3 schematizes the elimination of undesired binding of FlAsH-EDT$_2$ (Lumio™ Green) to vicinal cysteines, with retention of desired binding of the fluorophore to the engineered tetracysteine motif, by reduction of the proteins in the sample in the presence of a thiol competitor, exemplified by betamercaptoethanol, according to one embodiment of the present invention.
Figure 4:
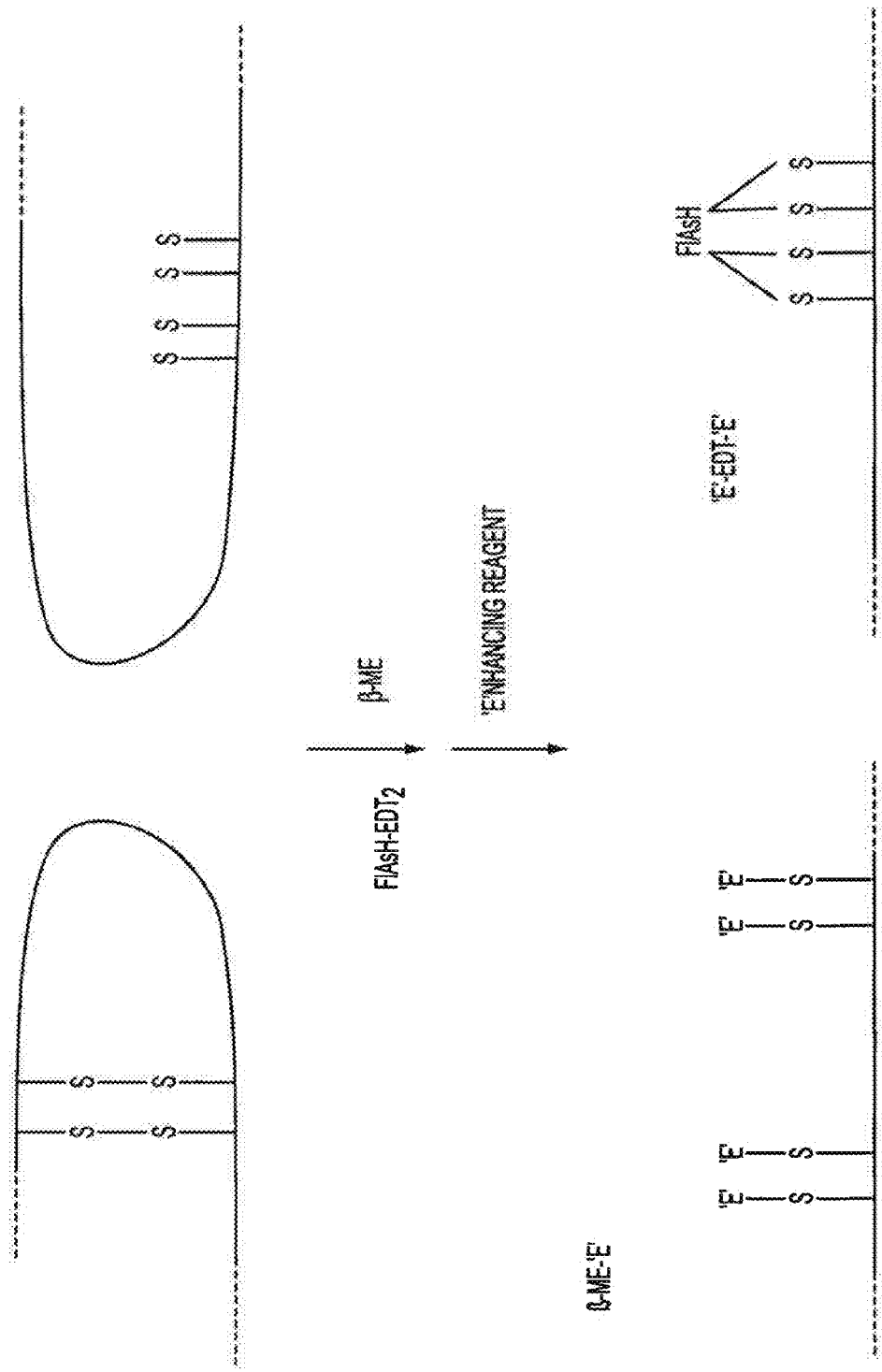
FIG. 4 schematizes a further embodiment of the methods of the present invention, in which a later incubation with a thiol-reactive blocking agent, such as a thiol-reactive capping agent, is used to prevent vicinal thiols from reacting with the biarsenical fluorophore after electrophoretic removal of the thiol competitor, exemplified by betamercaptoethanol, according to one embodiment of the present invention.

In a first aspect, the invention provides methods for labeling one or more tetracysteine-tagged proteins that are present in an inhomogeneous protein sample with biarsenical fluorophores; the methods provide increased specificity for labeling tetracysteine-tagged proteins over labeling proteins containing vicinal cysteines, thus decreasing spurious background fluorescence. The method comprises: reducing the proteins in the sample in the presence of a thiol competitor and a biarsenical fluorophore.

The protein to be labeled can be any protein having a tetracysteine peptide motif, CCXXCC (SEQ ID NO:1), wherein X is any amino acid.

In preferred embodiments, the tetracysteine tag has the sequence CCPGCC (SEQ ID NO:2). In some embodiments, the sequence Ala-Gly-Gly (AGG) is added to the N-terminus and Gly-Gly-Gly (GGG) added to the C-terminus of the CCPGCC (SEQ ID NO: 2) tag to minimize any interference with sequences and motifs bracketing the tetracysteine tag ("tetracysteine tag" and "FlAsH™-tag" are used synonymously herein; "FlAsH™-tag" is not intended to connote that the tag can be labeled only with FlAsH™ biarsenical fluorescein derivative) and better to present the tag as an epitope when generating antibodies against the tag. This 12 amino acid sequence, AGGCCPGCCGGG (SEQ ID NO:3), can be encoded by a nucleotide sequence optimized for expression in the desired host cell, as further described below, such as the nucleic acid sequence: 5'-GCT GGT GGC TGT TGT CCT GGC TGT TGC GGT GGC GGC (SEQ ID NO.: 4).

Cysteine tags that have fewer or more than 4 cysteines can also be used (e.g., 2, 3, 4, 5 or 6 cysteines). Typically, the intervening Xaa amino acids have a high propensity to form α-helical structures. A cysteine tag may be arranged such that the side chains of two pairs of cysteines are exposed on the same face of an α-helix. A cysteine tag need not be completely helical to react with a biarsenical reagent. For example, and without intending to be bound by theory, reaction of a first arsenic of a biarsenical with a pair of cysteines may nucleate an α-helix and position two other cysteines favorably for reacting with a biarsenical molecule.

The tetracysteine peptide tag is typically recombinantly fused to the protein desired to be labeled, either at the N-terminus, C-terminus, or in frame within the protein sequence; expression vectors for creating tetracysteine-fused recombinant proteins may readily be constructed using art-routine procedures.

In addition to the tetracysteine tag, other protein sequences can usefully be recombinantly appended to the proteins desired to be labeled. Among such additional protein sequences are linkers—so as to space the tetracysteine tag at a sufficient distance from critical residues of the protein to be labeled as to permit its proper folding, either for retention of biological function or immunogenicity, or both—and other short tags, usefully epitope tags, such as a FLAG tag, or a myc tag. Other sequences usefully included in the protein fusion include short tags useful for purification, such as a polyhistidine (e.g., 6Xhis (SEQ ID NO: 5)) tag.

In other embodiments, the tetracysteine tag is chemically conjugated to the protein to be labeled using art-routine conjugation chemistries.

The protein desired to be labeled can include a single tetracysteine tag or a plurality of tetracysteine tags; in embodiments in which the protein includes a plurality of recombinantly fused tags, the tags may be separated from one another within the primary amino acid sequence of the protein or directly multimerized in tandem.

The protein to which the tetracysteine tag is fused or conjugated can be any protein desired to be labeled, either naturally-occurring or nonnaturally occurring. Naturally-occurring proteins may have known biological function or not, and may be known to be expressed or only predicted from genomic sequence. The protein, if naturally-occurring, can be a complete protein or only a fragment thereof.

The tetracysteine-tagged protein desired to be labeled can thus be an animal protein, such as a human protein or non-human mammalian protein, a fungal protein, a bacterial protein, including eubacterial and archaebacterial protein, a plant protein, an insect protein or a viral protein.

The sample can be any protein sample in which the tetracysteine-tagged protein is present.

In one series of embodiments, for example, the tetracysteine-tagged protein is expressed recombinantly in host cells. In such embodiments, the sample is typically a lysate of the host cells. The lysate can be unpurified, partially purified, or substantially purified.

For example, the host cells can be bacterial host cells. Suitable bacterial host cells include gram negative and gram positive bacteria of any genus, including *Escherichia* sp. (e.g., *E. coli*), *Klebsiella* sp., *Streptomyces* sp., *Streptococcus* sp., *Shigella* sp., *Staphylococcus* sp., *Erwinia* sp., *Klebsiella* sp., *Bacillus* sp. (e.g., *B. cereus, B. subtilis* and *B. megaterium*), *Serratia* sp., *Pseudomonas* sp. (e.g., *P. aeruginosa* and *P. syringae*) and *Salmonella* sp. (e.g., *S. typhi* and *S. typhimurium*). Suitable bacterial strains and serotypes suitable for the invention can include *E. coli* serotypes K, B, C, and W. A typical bacterial host is *E. coli* strain K-12.

Host cells can be fungal host cells (such as *Saccharomyces cerevisiae* cells), insect cells, plant cells, or mammalian cells (including human cells).

In other embodiments, the tetracysteine-tagged protein is expressed in vitro, in which case the sample is the cell-free extract in which translation (and, optionally, transcription) is performed, or a partially purified or purified fraction thereof. In embodiments in which the extract permits coupled transcription and translation in a single cell-free extract, such as the *E. coli*-based ExpressWay or ExpressWay Plus systems (Invitrogen Corp., Carlsbad, Calif.), the sample is the cell-free extract in which transcription and translation commonly occur, or a fraction thereof.

Usefully, such in vitro transcription/translation extracts lack the SlyD polypeptide, which has been shown to interact with biarsenical reagents; in some embodiments, such extracts are prepared from host strains engineered to lack the SlyD polypeptide, such as the following exemplary strains deposited in the Agricultural Research Service Patent Culture Collection maintained by the National Center for Agricultural Utilization Research in Peoria, Ill., USA, as shown in Table 1.

TABLE 1

| Strain | Genotype | Accession No. |
| --- | --- | --- |
| JDP670 | F⁻ ompT hsdS$_B$ (r$_B$⁻m$_B$⁻) gal dcm slyD::kan (DE3) | B-30688 |
| JDP671 | F⁻ araD139 delta(argF-lac)U169 prsL150 relA1 deoC1 rbsR fthD5301 fruA25 slyD1 Tn10 (Tet⁻R) lambda– | B-30689 |
| JDP687 | Hfr rna-19 gdhA2 his-95 relA1 spoT1 metB1 slyD1 Tn10 (Tet⁻R) | B-30690 |
| JDP689 | Hfr rna-19 gdhA2 his-95 relA1 spoT1 metB1 slyD::kan | B-30691 |
| JDP694 | F⁻ ompT hsdS$_B$ (r$_B$⁻m$_B$⁻) gal dcm slyD1 (DE3) | B-30692 |
| JDP704 | F⁻ ompT hsdS$_B$ (r$_B$⁻m$_B$⁻) gal dcm rne131 slyD1 (DE3) | B-30693 |
| JDP707 | F⁻ ompT hsdS$_B$ (r$_B$⁻m$_B$⁻) gal dcm rne131 slyD::kan (DE3) | B-30694 |

In vitro transcription/translation extracts derived from such slyD mutant strains are further described in commonly-owned U.S. patent application Ser. No. 10/954,951 (Hanson et al., "Compositions and Methods for Synthesizing, Purifying and Detecting Biomolecules," filed Oct. 1, 2004, now abandoned); and commonly-owned U.S. provisional application No. 60/508,142 (Hanson, "Compositions and Methods for Purifying and Detecting Biomolecules," filed Oct. 1, 2003, now expired), the disclosures of which are incorporated herein by reference in their entireties. Other in vitro transcription/translation systems suitable for use with the present invention are further described in commonly-owned U.S. provisional application No. 60/614,590 (Kudlicki et al., "Feeding Buffers, Systems, and Methods for In Vitro Synthesis of Biomolecules," filed Oct. 1, 2004, now expired), the disclosure of which is incorporated herein by reference in its entirety.

Moreover, proteins can be tagged using a motif taken from or based on the slyD sequence, such that the tagged protein can bind biarsenical fluorophores. Such slyD-tagged proteins can also be used with the present invention to achieve labeling with increased specificity. Such slyD-based tags are further described in commonly-owned U.S. patent application Ser. No. 10/970,635 entitled "Target Sequences for Synthetic Molecules" (Hanson, filed Oct. 22, 2004, now abandoned) the disclosure of which is incorporated herein by reference in its entirety.

Such slyD strains are not required, however, since the methods, compositions, and kits of the present invention improve specificity of labeling of tetracysteine-tagged proteins even in the presence of SlyD and similar cysteine-rich proteins.

In the methods of the present invention, the proteins in the sample are treated in the presence of a composition comprising thiol competitor and a biarsenical fluorophore. The thiol competitor may serve additionally as a reducing agent. In some embodiments of the present invention, the composition may further comprise an additional reducing agent in addition to the thiol competitor.

Reducing agents usefully include dithiothreitol (DTT), tris (2-carboxyethyl)phosphine (TCEP), tri-n-butylphosphine (TBP), 2-mercaptoethanol (2-ME or β-ME), and mercaptoethanesulfonic acid (MES), and combinations thereof. Other reducing agents may also be used.

The reducing agents are usefully present in concentrations of at least about 10 μM, typically at least about 100 μM, 1 mM, 2.5 mM, 3.75 mM, 5 mM, 10 mM, 50 mM, 100 mM, even at least about 350 mM, and in concentrations typically no more than about 500 mM, more typically no more than about 350 mM, 200 mM, 100 mM, often no more than about 50 mM, 10 mM, 5 mM, 2.5 mM, even on occasion no more than about 100 μM or even 10 μM.

Thiol competitors, as defined herein, are compounds that are useful for competing with other thiol functional groups, such as those found in vicinal cysteines, for binding to biarsenical fluorophores. In some embodiments, the thiol competitors usefully may have a higher, similar, or lower affinity with the biarsenical fluorophores than the non-specific thiol groups, such as those found in slyD. In some embodiments, the thiol competitor may have a lower affinity to the biarsenical fluorophore than the specific tetracysteine tag described herein.

Thiol competitors usefully include 2-mercaptoethanol (2-ME or β-ME), 1-mercaptopropanol, 2-mercaptopropanol, 1-mercaptobutanol, 2-mercaptobutanol, mercaptoethanesulfonic acid (MES), 1-mercapto-1,2-propanediol (MPD), mercaptoacetic acid, mercaptosuccinic acid, 3-mercaptopropionic acid, cysteine, cys-cys dipeptide, 2,3-dimercapto-1-propanesulfonic acid (DMPS), meso-2,3-dimercaptosuccinic acid (DMS), 2,3-dimercapto-1-propanol (DMP), benzenethiol, and 4-methylbenzenethiol. Among mono- and dithiol competitors, at present monothiols are preferred to details. Other thiol competitors may also be used. It is understood that the foregoing thiol competitors may also act as reducing agents.

Thiol competitors (equivalently, "thiol binding competitors" or "competitors") are usefully present in concentrations of at least about 10 µM, typically at least about 100 µM, 1 mM, 2.5 mM, 5 mM, 10 mM, 50 mM, 100 mM, even at least about 350 mM, 400 mM, even at least about 450 mM or 500 mM, and in concentrations typically no more than about 500 mM, more typically no more than about 350 mM, 200 mM, 100 mM, often no more than about 50 mM, 10 mM, 5 mM, 2.5 mM, even on occasion no more than about 100 µM or even 10 µM.

In preferred embodiments, the thiol competitor is itself a reducing agent.

In one such embodiment, the thiol competitor is β-ME, usefully in a concentration of greater than about 1 mM, often at a concentration of greater than about 2 mM, 3 mM, 4 mM, even greater than about 5 mM. In some embodiments, β-ME is present at a concentration of greater than about 10 mM, 20 mM, 30 mM, and may be present in a concentration of 40 mM, 50 mM, 60 mM, 65 mM, 70 mM, even 100 mM, 200 mM, 300 mM or higher, with intermediate values permissible. In some embodiments, the thiol competitor is β-ME at a concentration of no more than about 500 mM, typically no more than about 450 mM, 400 mM, 350 mM, 300 mM, 250 mM, 200 mM, 150 mM, even no more than about 100 mM.

In another series of embodiments, the reducing agents are TBP and β-ME, with β-ME serving additionally as a thiol competitor. In these latter embodiments, the TBP can usefully be present in a concentration of at least about 1 mM, 2 mM, 3 mM, 4 mM, 5 mM, even at least about 10 mM, and typically less than about 10 mM, 5 mM, and often at about 3-5 mM, with intermediate values, such as 4 mM, permissible and useful.

In the presence of TBP, β-ME can usefully be present at a concentration of at least about 5 mM, 10 mM, 15 mM, 20 mM, 25 mM, 30 mM, even at least about 35 mM, 40 mM, 45 mM, 50 mM, 55 mM, 60 mM, 65 mM, even 70 mM or more, and typically at a concentration of less than about 100 mM, 95 mM, 90 mM, 85 mM, 80 mM, with intermediate values permissible and a concentration of about 70 mM proving useful.

In some embodiments, the thiol competitor is a monothiol, usefully at a concentration greater than about 5 mM, often at a concentration greater than about 20 mM, 50 mM, even greater than about 100 mM. In other embodiments, the thiol competitor is a dithiol, usefully at a concentration of about 100 µM, 200 µM, 300 µM, 400 µM, 500 µM, even at least about 1 mM, 1.5 mM, 1.75 mM, 2 mM, 5 mM, or 10 mM or higher.

In the methods of the present invention, the biarsenical fluorophore can usefully be a biarsenical derivative of a known fluorophore, such as fluorescein, usefully FlAsH-EDT$_2$ (Lumio™ Green, Invitrogen Corp., Carlsbad, Calif.), or such as resorufin, usefully ReAsH-EDT$_2$ (Lumio™ Red, Invitrogen Corp., Carlsbad, Calif.), or may instead be an oxidized derivative, such as ChoXAsH-EDT$_2$ or HoXAsH-EDT$_2$.

The biarsenical fluorophore can be a biarsenical derivative of other known fluorophores, including, e.g., the Alexa fluor series, as described in U.S. Pat. No. 6,130,101, incorporated herein by reference in its entirety, including Alexa Fluor-350, Alexa Fluor-430, Alexa Fluor-488, Alexa Fluor-532, Alexa Fluor-546, Alexa Fluor-568, Alexa Fluor-594, Alexa Fluor-663 and Alexa Fluor-660, available commercially from Molecular Probes (Eugene, Oreg.).

The biarsenical fluorophore can be any of the biarsenical fluorophores described in U.S. Pat. No. 6,054,271, incorporated herein by reference in its entirety.

The biarsenical fluorophore can be present at a concentration of at least about 1 µM, 2 µM, 3 µM, 4 µM, 5 µM, 10 µM, 20 µM, 30 µM, 40 µM, 50 µM, 100 µM or more, and at a concentration of no more than about 500 µM, 400 µM, 300 µM, 200 µM, 100 µM, 90 µM, 80 µM, 70 µM, even no more than about 60 µM, 50 µM, or even no more than about 40 µM, with intermediate values permissible. For FlAsH-EDT$_2$ (4'-5'-bis(1,3,2-dithioarsolan-2-yl)fluorescein-(2,2-ethanedithiol)$_2$), the concentration can usefully be at least about 5 µM, 10 µM, 20 µM, 30 µM, 40 µM, 50 µM, often no more than about 100 µM, 90 µM, 80 µM, 70 µM, 60 µM, 50 µM, 40 µM, with intermediate values permissible and useful, and with a concentration of about 10 µM being particularly useful.

The order of addition of reducing agent, thiol competitor, and biarsenical fluorophore is not critical.

Typically, the reducing agent and thiol competitor are added to the protein sample prior to addition of biarsenical fluorophore. In some embodiments, the reducing agent and thiol competitor are separate agents commonly included in a single fluid composition, and are thus added simultaneously to the protein sample. In other embodiments, the reducing agent and thiol competitor are present as separate compounds (or, if liquid, neat) or in separate compositions, and are added separately, in either order, to the protein sample. In other embodiments, the reducing agent and the thiol competitor are the same.

In yet other embodiments, the biarsenical fluorophore is added before, or concurrently with, one or both of the reducing agent and thiol competitor.

Optionally, treatment of the proteins in the sample by incubation in the presence of a thiol competitor (and, optionally, also the biarsenical fluorophore) is carried out at temperatures above room temperature, such as at a temperature of at least about 30° C., 40° C., 50° C., even at least about 60° C., 70° C., or 80° C., even as high as 90° C., 95° C., 96° C., 97° C. even as high as 100° C., with intermediate values permissible, and typically at a temperature no more than about 97° C., 96° C., 95° C., 90° C., 80° C., even no more than about 70° C., with intermediate values permissible. As further described in Example 1, below, a temperature of 70° C. usefully accelerates the reductive labeling, in the presence of a thiol competitor, of the tetracysteine-tagged protein desired to be labeled.

Incubation can also be performed at room temperature. In such embodiments, the incubation period is usefully increased. The duration of incubation can readily be determined by observing the increase in fluorescence over time, and determining the timepoint beyond which fluorescence does not increase.

Additional agents may usefully be added to the protein sample, including: density-adjusting agents, such as sugars and polysaccharides, including glycerol or sucrose; buffering agents, such as Tris base and Tris HCl; detergents, such as sodium dodecyl sulfate (SDS) or lithium dodecylsulfate (LDS); chelating agents, such as EDTA or EGTA; and visually detectable dyes, such as Serva Blue G or bromophenol blue, with such visually detectable dyes typically chosen so as not to absorb significantly at the emission maximum of the biarsenical fluorophore.

The sample proteins are reductively incubated with the thiol competitor and biarsenical fluorophore for at least 30 seconds, typically at least 1 minute, more typically at least 2 mins, 3 mins, 4 mins, 5 mins, even 6, 7, 8, 9, 10 minutes, with times of at least 20 mins, 30 mins, 40 mins, 50 mins, even at least 1 hour, and times intermediate thereto, permissible. In some embodiments, the sample proteins can be reductively incubated with the thiol competitor and biarsenical fluorophore for at least about 2 hours, 3 hours, even at least about 4 hours or more.

Typically, the sample proteins are reductively incubated (i.e., incubated in the presence of a reducing agent) in the presence of a thiol competitor and biarsenical fluorophore for fewer than about 5 hours, 4 hours, 3 hours, 2 hours, even less than 1 hour, particularly when incubation is optionally performed at temperatures above room temperature, as described below. Times intermediate thereto are also permissible.

The duration of reductive incubation in the presence of a thiol competitor and biarsenical fluorophore is typically not critical, and may be conveniently adjusted to the needs of the experiment.

As shown in the exemplary methods of Example 1, reductive incubation in the presence of a thiol competitor and biarsenical fluorophore can usefully be performed at 70° C. in as few as 10 minutes. As further shown in Example 1, the protein sample can thereafter be allowed to cool, typically to room temperature, when reductive incubation in the presence of a thiol competitor and biarsenical fluorophore is performed at elevated temperature.

In some embodiments of the methods of the present invention, a control protein may usefully be labeled to monitor the effectiveness of biarsenical fluorophore labeling, either in a parallel reaction or, if readily resolvable from the protein desired to be labeled, by inclusion in the same reaction.

In one such embodiment, particularly useful as a control for labeling with a biarsenical derivative of fluorescein, such as FlAsH™ (Lumio™ Green, Invitrogen Corp., Carlsbad, Calif.), the control protein can usefully be tetracysteine-tagged cyan fluorescent protein (CFP), effective labeling of which can be monitored as a decrease in fluorescence emission at 485 nm upon excitation at about 430 nm, the emission maximum of native CFP, with concomitant increase in emission at 535 nm due to fluorescence resonance energy transfer between the CFP and covalently bound FlAsH™ molecule.

The methods of the present invention significantly reduce the spurious binding of the biarsenical fluorophore to proteins lacking the tetracysteine tag without significantly reducing the binding of the biarsenical fluorophore to proteins having the tetracysteine tag, substantially increasing specificity of binding of biarsenical fluorophores to tetracysteine tags.

As shown in FIGS. 5A-5B, 6A-6B, 7A-7B, and 8A-8B, and further demonstrated in the Examples below, the methods of the present invention may readily be used to label, with high specificity, a wide range of tetracysteine-tagged proteins that are expressed in E. coli, that are expressed in mammalian cells, and that are expressed in vitro in a coupled transcription-translation cell-free extract, with high signal and high specificity.

As also shown in FIGS. 5-8, the methods of the present invention find particular use in labeling tetracysteine-tagged proteins that are subsequently to be resolved by polyacrylamide gel (PAGE) electrophoresis, permitting the in-gel detection of tetracysteine-tagged proteins without gel drying, without blotting, and without expensive and complex equipment.

Thus, in another series of embodiments, the methods of the present invention can usefully include a subsequent step of resolving the sample proteins by electrophoresis, such as gel electrophoresis, capillary electrophoresis, or fluid (solution) phase electrophoresis.

For size fractionation, the labeled proteins can be resolved, for example, by gel electrophoresis, for example by electrophoresis in a 10% Bis-Tris gel, a 4-12% Bis-Tris gel, or a 12% Bis-Tris Gel, such as a NuPAGE® Novex Bis-Tris gel (Invitrogen Corp., Carlsbad, Calif.) run with either MES or MOPS buffer. In other such embodiments, the proteins can be resolved in a Tris-acetate (TA) gel, such as a 7% or 3-8% gradient Tris-acetate gel, such as a NuPAGE® Novex Tris acetate gel (Invitrogen Corp., Carlsbad, Calif.). In yet other embodiments, the proteins can be resolved in a Tris-glycine (TG) gel, including 4% TG gels, 6% TG gels, 8% TG gels, 10% TG gels, 12% TG gels, 14% TG gels, 16% TG gels, and 18% TG gels, and TG gels having gradients such as 4-12%, 4-20%, 8-16%, 10-20%, such as the TG gels available from Invitrogen Corp. (Carlsbad, Calif.). In yet other embodiments, the proteins can be resolved in Tricine gels, such as 10% Tricine gels, 16% Tricine gels, or even 10-20% gradient Tricine gels, and in standard Laemmli gels.

The gel-based electrophoretic embodiments of the methods of the present invention can be carried out in gels of any suitable physical format, for example in standard-sized gels, minigels, strips, in gels designed for use with microtiter plates and in other high throughput (HTP) applications.

For example, up to 96 protein samples labeled according to the methods of the present invention can be resolved simultaneously in an E-PAGE™ High-Throughput (HTP) Protein Electrophoresis System (Invitrogen Corp., Carlsbad, Calif.). The E-PAGE™96 gels are self-contained, pre-cast gels that include a gel matrix and electrodes packaged inside a disposable, UV-transparent cassette. Each E-PAGE™ 96 gel contains 96 sample lanes and 8 marker lanes in a staggered well format. The well openings of the E-PAGE™ 96 cassette are compatible with the standard 96-well plate format and can be conveniently loaded with a multichannel pipettor or 8-, 12-, or 96-tip liquid-handling robotic devices. In addition, each E-PAGE™ 96 cassette is labeled with an individual barcode to facilitate identification of the gel using commercial barcode readers. The E-PAGE™ gel matrix is further described in commonly owned provisional patent application Nos. 60/504,683, filed Sep. 19, 2003, now expired; 60/508,786, filed Oct. 2, 2003, now expired; 60/560,310, filed Apr. 6, 2004, now expired; and U.S. patent application Ser. No. 10/946,472 (Updyke et al., "Composite Compositions for Electrophoresis," filed Sep. 20, 2004), the disclosures of which are incorporated herein by reference in their entireties.

Gel formats within which the labeled proteins of the present invention may usefully be resolved include without limitation those described in the following patents and published patent applications: U.S. Pat. Nos. 5,578,180; 5,922,185; 6,059,948; 6,562,213; 6,057,106; 6,096,182; 6,143,154; 6,162,338; U.S. Patent application publication nos. 2002/0134680 A1; 2003/0127330 A1; and 2003/0121784 A1; and published PCT Application Nos. WO 95/27197, WO 99/37813, WO 02/18901, WO 02/071024, the disclosures of which are incorporated herein by reference in their entireties.

The embodiments of the present invention that include electrophoretic separation of biarsenically labeled proteins may also be practiced using capillary electrophoresis (CE) or capillary zone electrophoresis (CZE).

For fractionation based on isoelectric point, the proteins can be resolved using isoelectric focusing (IEF), either as a single separation step or as a step preliminary to size fractionation (i.e., as the first step in 2D-PAGE).

For example, the labeled proteins can be resolved using solution phase isoelectric focusing. Zuo et al., *Anal. Biochem.* 284: 266-278 (2000); Zuo et. al., *Electrophoresis* 22: 1603-1615 (2001); Zuo et al., *Proteomics:* 2: 58-68 (2002); Zuo et al., *Journal of Chromatography B* 782: 253-265 (2002); Ali-Khan et al., *Current Protocols in Protein Science* 22.1: 1-19 (2002), the disclosures of which are incorporated herein by reference in their entireties. Devices and kits for fluid phase isoelectric focusing are available commercially (ZOOM® IEF Fractionator, Invitrogen Corp., Carlsbad, Calif.). In such embodiments, the proteins can be labeled with biarsenical fluorophore before or after fractionation with solution phase IEF.

In other embodiments, the labeled proteins can be resolved using gel-based isoelectric focusing, either in slab gels, in tube gels, or, in one series of embodiments, in immobilized pH gradient (IPG) strips.

IPG strips are available commercially (Zoom® IPG strips, Invitrogen Corp., Carlsbad, Calif.). Devices that substantially facilitate their usage have recently been described—e.g., in commonly owned international patent application published as WO 02/092200, concurrently pending and commonly owned U.S. Pat. Appl. Publ. No. 2003/0015426, and commonly owned U.S. Pat. No. 7,601,251, the disclosures of which are incorporated herein by reference in their entireties. Such devices are available commercially (Zoom® IPGRunner™ system, Invitrogen Corp., Carlsbad, Calif.).

Although the methods above-described for labeling tetracysteine-tagged proteins can usefully be followed, in a wide variety of embodiments, by a subsequent step of electrophoresis, we have found that the resulting increase in labeling specificity using the methods of the present invention can surprisingly be lost during some types of gel electrophoresis, particularly polyacrylamide gel electrophoresis in neutral pH gels.

Without intending to be bound by theory, it appears that the neutral pH of certain gels—such as the long shelf life, prior-cast, high resolution NuPAGE™ bis-tris gels—precludes significant migration into the gel of uncharged mono- and di-thiol thiol competitors; comigration of the biarsenical fluor and sample proteins in the gel in the absence of such thiol competitors permits the biarsenical fluorophores to bind to vicinal thiols that had earlier been blocked by the thiol competitors.

Accordingly, in some embodiments of the methods of the present invention, a blocking agent may usefully be added after the step of reductive incubation with thiol competitor and biarsenical fluorophore, and before further analytical or preparative steps, such as resolution by electrophoresis. Without intending to be bound by theory, it is believed that the blocking agent caps vicinal thiols and prevents binding of the fluor to those thiols during electrophoresis.

The blocking (equivalently herein, "enhancing") agent may usefully be an agent capable of alkylating, or otherwise covalently capping, free sulfhydryls.

The blocking agent can thus be an alkylating agent, such as an acylhalide or alkylhalide, such as a haloacetamide, such as iodoacetamide or iodoacetic acid; a dithiol that will form a stable disulfide bond with sulfhydryls, such as dithiobis(2-nitrobenzoic acid) (DTNB), dithiobis(5-nitropyridine); or a maleimide, such as maleimide or ethylenemaleimide. Other blocking agents include Ellman's reagent and methyl triflate.

Other useful blocking agents include, for example, 4-vinylpyridine, acrylamide, dimethylacrylamide, and others.

One disadvantage of iodoacetamide as a blocking agent in the methods of the present invention is that it is difficult to solubilize at high concentrations in water. Accordingly, in embodiments in which iodoacetamide is used as the blocking reagent, it is preferably solubilized in other solvents, such as dimethylformamide, dimethylsulfoxide, isopropanol, acetonitrile, ethanol, and methanol, with methanol currently preferred for high concentration stock solutions.

The sample is typically incubated in the presence of blocking agent for at least 1 minute, 2 mins, 3 mins, 4 mins, even at least 5 mins, with incubation times of 10 mins, 20 mins, even 30 mins, 60 mins, or 2 hrs or more possible, with times intermediate thereto permissible. Incubation in the presence of blocking reagent can usefully be fewer than 60 mins, 50 mins, 40 mins, even fewer than 30 mins. As shown in the embodiments of Example 1, an incubation of no more than 5 minutes is useful.

Typically, incubation in the presence of blocking reagent is performed at room temperature, although incubation at elevated or reduced temperature also be performed.

Surprisingly, a lower concentration of blocking agent than would be expected to be required, based upon the concentration of concurrently present thiol competitor, can be used effectively. Thus, if the thiol competitor is βME at a concentration of 100 mM, 90 mM, 80 mM, even 70 mM, effective concentrations of blocking reagent, such as maleimide, DTNB or iodoacetamide, can be as low as 100 mM, 75 mM, 50 mM, 40 mM, even as low as 25 mM.

Addition of the blocking reagent leads to a substantial improvement in specificity of labeling of tetracysteine-tagged proteins in neutral pH gels.

In embodiments in which the labeled proteins are resolved by electrophoresis, the methods may usefully include a further step of visualizing the labeled proteins.

Such visualization can usefully be done with the proteins still present in an intact gel (in-gel detection), by exciting the fluorophore using a UV transilluminator or a laser-based scanner.

For example, in embodiments in which the biarsenical fluorophore is a fluorescein derivative, such as Lumio™ Green (FlAsH™), the gel can be placed on a UV transilluminator equipped with a standard camera having either an ethidium bromide or SYBR® Green-appropriate filter. Alternatively, a laser-based scanner can be used, such as the Typhoon™ or Storm™ Scanners (Amersham Biosciences, Piscataway, N.J.), using a laser line that falls within the excitation maximum of the fluorophore (500 nm), and a 535 nm long pass filter or band pass filtered centered near the emission maximum of 535 nm.

Optionally, the gel is first removed from the cassette; depending upon the UV-attenuating characteristics of the cassette materials, removal of the gel can increase sensitivity of detection.

Using the methods and compositions of the present invention, proteins can be detected in electrophoresis gels with high sensitivity. The methods and compositions permit detection of no more than about 1 pMol tetracysteine-tagged protein, more typically detection of no more than about 5 pMol protein, and can detect 10 pMol, 25 pMol or more. The methods and compositions of the present invention can detect as little as 1 ng of tagged protein, 2 ng, 3 ng, 4 ng, even as little as 5 ng protein.

In one series of embodiments, the proteins of the labeled sample can usefully be resolved in parallel with a series of fluorescent molecular weight standards.

Usefully, the standards are spectrally matched to the biarsenical fluorophore used to label the proteins. Such spectral matching can be accomplished, for example, by using tetracysteine-tagged protein standards that are labeled in parallel with the same biarsenical fluorophore used to label the protein sample, or by using standards having a fluorescent moiety that is spectrally matched to the biarsenical fluorophore used to label the sample proteins. Examples of standards useful in the practice of the present invention include the Benchmark™ family of protein standards (Invitrogen Corp., Carlsbad, Calif.).

Such spectral matching permits the standards to be excited at a wavelength that commonly excites the biarsenical fluorophore, and further permits the fluorescence emission of the standards to be commonly detected with that of the biarsenically-labeled sample proteins.

In some embodiments, the tetracysteine-tagged protein can be eluted from the gel following in-gel visualization of the biarsenical fluorophore and then further analyzed or purified. In some of these latter embodiments, the biarsenical fluorophore is released from the tetracysteine-tagged protein, typically using 1,2-ethanedithiol (EDT), dithiothreitol (DTT), or 2,3-dimercaptopropanesulfonate (DMPS).

The methods, compositions and kits of the present invention can also be used to increase specificity of binding by biarsenical fluorophores to tetracysteine-tagged proteins for purposes other than gel electrophoresis.

For example, the methods, compositions, and kits of the present invention may be used to increase the specificity of tetracysteine labeling for quantitation of yield of in vitro synthesized protein. In such embodiments, aliquots can be withdrawn periodically from the in vitro translation (in particularly useful embodiments, from the coupled transcription-translation) reaction, the translation reaction stopped, and the sample then reduced in the presence of a thiol competitor and biarsenical fluorophore, and optionally thereafter with thiol-blocking reagent, according to the methods of the present invention. In a subsequent step, the amount of fluorescence is quantitated, as by fluorometry.

In in vitro translation (and, in particularly useful embodiments, in coupled transcription-translation) systems that tolerate the presence of thiol competitor at concentrations effective in the methods of the present invention, monitoring of tetracysteine-labeled protein synthesis can be performed in real-time, without taking aliquots. In such case, the duration of incubation in the presence of reducing agent, thiol competitor, and biarsenical fluorophore vary continuously as well.

Figure 9:
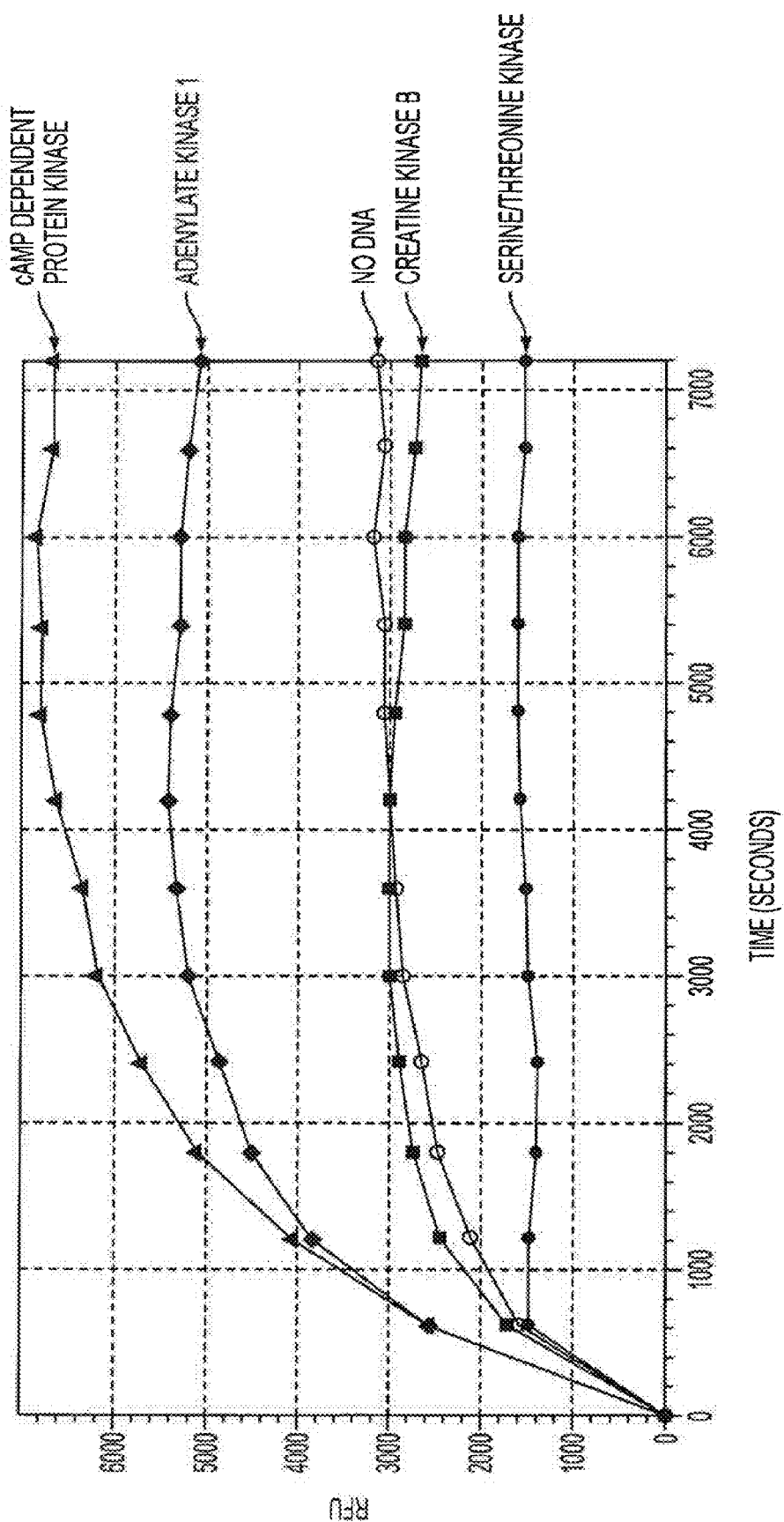
FIG. 9 shows real-time detection of tetracysteine-tagged protein production, using Lumio™ Green labeling of in vitro synthesized tetracysteine-tagged protein.

An example of such real-time measurement, albeit without addition of the thiol competitor or blocking reagents according to the methods of the present invention, is presented in Example 4 and FIG. 9.

Real-time monitoring of protein expression usefully enables confirmation of protein expression without gels, evaluation of transcription/translation regulators, screens for expression. Moreover, these and other real-time monitoring methods may be performed in a high throughput manner.

As another example, the methods of the present invention can increase the specificity of purification of tetracysteine-tagged proteins using biarsenical affinity supports, such as the FlAsH™ affinity resin described in Thorn et al., "A novel method of affinity-purifying proteins using a bis-arsenical fluorescein," *Protein Sci.* 9:213-217 (2002), the disclosure of which is incorporated herein by reference in its entirety. In such embodiments, the biarsenical compound does not need to be a biarsenical derivative of a fluorophore; it can be any biarsenical with spacing suitable for binding to a tetracysteine motif.

In a typical embodiment, a protein sample having a tetracysteine-tagged protein desired to be purified is reductively incubated with a thiol competitor and with a biarsenical moiety (either with or without a fluorophore) that is attached, often covalently, to a support.

The support may include one or more surfaces of a unitary object, such as a slide, dipstick, microtiter plate well, MALDI source, or SELDI source, or may instead comprise the surfaces of a plurality of discrete objects, such as beads.

The support may be glass, although other solid materials, such as metal, amorphous silicon, crystalline silicon, or plastics, may also be used. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, and mixtures and copolymers thereof.

The support may be a surface of a bead, or pellet. The beads may be of substantially spherical geometry, but need not be limited to such. In addition, the beads may be porous or otherwise permit access to its interior spaces and surfaces, thus increasing the available surface area of the bead available for purification. Bead dimensions usefully range from nanometers, e.g. 100 nm, to millimeters, e.g. 5 mm, usefully from about 0.2 micron to about 200 microns, with beads having dimensions from about 0.5 to about 5 microns being typical.

Suitable bead compositions include polymers often used in affinity chromatography, such as agarose beads, or controlled pore glass, plastics, such as polystyrene, methylstyrene, acrylic polymers, ceramics, glass, paramagnetic materials, titanium dioxide, latex, cross-linked dextrans, cellulose, and nylon. See, e.g., "Microsphere Detection Guide" (Bangs Laboratories, Inc.).

Usefully, the beads are magnetic, paramagnetic, or superparamagnetic, permitting separation of the beads from the liquid sample by application of a suitable magnetic field. A variety of such beads may be purchased commercially from Dynal® Biotech Inc. (Lake Success, N.Y.) and Miltenyi Biotec Inc. (Auburn, Calif.), and biarsenical fluorophores conjugated thereto using standard chemistries, such as that described in Thorn et al., "A novel method of affinity-purifying proteins using a bis-arsenical fluorescein," *Protein Sci.* 9:213-217 (2002).

In some embodiments, the support comprises a plurality of beads, optionally magnetic, paramagnetic, or superparamagnetic, the beads further comprising a bead-purification moiety. The bead-purification moiety may, for example, be one member of a high affinity binding pair, such as biotin or streptavidin, permitting the beads (and tetracysteine-tagged protein bound thereto) subsequently to be purified using the other member of the binding pair.

In some embodiments, the purification methods include a further step of adding a blocking (enhancing) agent, as described herein, after the step of reductive incubation with thiol competitor and support-bound biarsenical fluorophore.

In yet other embodiments, the support comprises a gel or resin, and the biarsenical fluorophore-bound gel or resin is retained within a column, usefully a column having chemicophysical properties that ensure low nonspecific protein adsorption to the column itself.

In such embodiments, the reducing agent, thiol competitor, biarsenical fluorophore, and optional thiol blocking agent may usefully be selected from those described above. Analogously, incubation times and concentrations of reducing agent, thiol competitor, biarsenical fluorophore, and optional thiol blocking agent are usefully substantially similar to those described above.

In some embodiments, the thiol competitor is added to the sample prior to contact of the sample to the biarsenical affinity resin or gel. In other embodiments, the thiol competitor is included in the column equilibration buffer. In yet other embodiments, the thiol competitor is included both in the sample prior to contact of the sample to the affinity resin or gel and is additionally included in the column equilibration buffer.

The purification methods typically further comprise a step of removing the support from the protein sample, or equivalently, of removing the protein sample from the support, as by washing the solid support to remove nonspecifically bound proteins.

The purification methods may further comprise a subsequent step of releasing the tetracysteine-tagged protein from the biarsenical fluorophore support. Typically, release is effected using 1,2-ethanedithiol (EDT), dithiothreitol (DTT), 2,3-dimercaptopropanesulfonate (DMPS).

Purification of tetracysteine-tagged proteins using the methods of the present invention can achieve protein purities of at least about 70%, 75%, 80%, 85%, 90%, 95%, even 96%, 97%, 98% or even more by weight.

The methods and compositions of the present invention can also be used to quantitate the amount of tetracysteine-tagged protein present in a sample.

In such embodiments, the methods of the present invention further comprise quantitating the amount of fluorescence from the biarsenical fluorophore.

The quantitation can be done without resolution of the proteins present in the protein sample or after the proteins have been partially or fully resolved, as by electrophoresis, such as PAGE, 2D-PAGE, or IEF. Fluorescence can be quantitated by, e.g., a fluorometer. Quantitation of the proteins can also be performed by absorption spectrometry.

In another aspect, the invention provides compositions useful in the practice of the methods of the present invention.

In one embodiment, the invention provides a composition comprising a reducing agent and a thiol competitor at concentrations useful in the practice of the methods of the present invention. In another embodiment, the composition further comprises a biarsenical fluorophore at a concentration useful in the practice of the methods of the present invention.

In some embodiments of the invention, the biarsenical fluorophore is prepared as a stable formulation. That is, the formulation can be stored at −80° C., −20° C., 4° C., ambient temperature or even higher temperatures for a period of time with little or no loss of function. Preferably, such formulations are stable for a period of time such as 2 years, 12 months, 6 months, 3 months, 60 days, 30 days or 2 weeks. A preferred stable formulation is one that may be used directly as a loading solution or a gel-staining solution, or as a stock solution that can be diluted in order to generate such solutions.

In yet another aspect, the invention provides a kit for use in the practice of the methods of the present invention.

In one series of embodiments, the kit provides a first composition comprising a biarsenical fluorophore, a separately packaged second composition comprising a reducing agent and a thiol competitor, and optionally a third composition comprising a blocking reagent. As described hereinabove, in some kit embodiments of the present invention the reducing agent and the thiol competitor may be the same agent.

The kits may include a plurality of one or more of the above-described compositions, and may further include compositions for effecting cell lysis, and compositions that can be diluted to serve as loading or running buffers for gel electrophoresis. In some embodiments, the kit further includes a separate composition comprising protein standards, such as protein standards whose fluorescence is spectrally-matched to that of the biarsenical fluorophore. In some kit embodiments, the included protein standards may be pre-labeled with the fluorophore, such as by the biarsenical fluorophore. Alternatively, or in addition, the kit may include protein standards that include a suitable motif, such as the tetracysteine motif, such that the protein standards can be labeled with a biarsenical fluorophore, such as by using the compositions already included with the kit.

In addition to a composition of the invention, a kit of the invention may comprise: one or more sets of instructions; one or more electrophoretic media, such a precast gel or compositions and materials for preparing gels; one or more antibodies that bind to a protein tag.

As described above, in some embodiments of the methods of the present invention, the biarsenical fluorophore can be covalently or noncovalently attached to a support, such as the supports described above. In embodiments in which the support is a plurality of magnetic, paramagnetic, or superparamagnetic beads, the kits of the present invention can usefully further comprise apparatus for magnetic separation of the beads within a fluid suspension.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

The examples presented herein provide exemplary instructions for the practice of some embodiments of the methods of the present invention.

Example 1

Exemplary Results with Tagged Proteins Expressed in *E. Coli*

Human glucuronidase beta (GUS), human kinase, and chloramphenicol acetyltransferase (CAT) were expressed as tetracysteine-tagged fusions in BL21 Star™ *E. coli* cells (Invitrogen Corp., Carlsbad, Calif.). Uninduced control samples, samples 2 hours post induction, and samples 4 hours post induction were lysed with BugBuster reagent (Novagen, Inc., Madison, Wis.) and processed for visualization of the tagged proteins.

Briefly, 5 µL of 4× labeling sample buffer was added to about 15 µL protein sample.

The 4× labeling sample buffer contains, per 10 ml: (i) 377 µL of 400 mM TBP stock solution (102.6 µL neat Tri-n-butylphosphine (Sigma-Aldrich) to 897.4 µL isopropanol), (ii) 185 µL beta mercaptoethanol (Sigma-Aldrich), and (iii) 9.43 ml 4× sample buffer (containing, per 10 ml, glycerol (4.0 g), Tris Base (1.364 g), Tris HCl (1.332 g), LDS (0.8 g), EDTA (0.006 g) and Serva Blue G (0.75 ml of 1% solution (SO-BLUE)).

To the protein sample was then added 0.2 µL of Lumio™ Green detection reagent. An exemplary detection reagent comprises 1 mM biarsenical fluorophore in a 90% DMSO solution. The sample was heated at 70° C. for 10 minutes, then centrifuged for 10 seconds to collect the condensate from the lid of the tube.

An aliquot of 2 μL of thiol-alkylating reagent was added and the sample incubated for five minutes at room temperature. An exemplary thiol-alkylating reagent comprises 1 M maleimide in DMSO solution.

Treated samples were then loaded on a 4-12% Bis-Tris NuPAGE® gel (Invitrogen Corp., Carlsbad, Calif.) and electrophoresed according to standard protocols with MES running buffer.

Figure 5B:
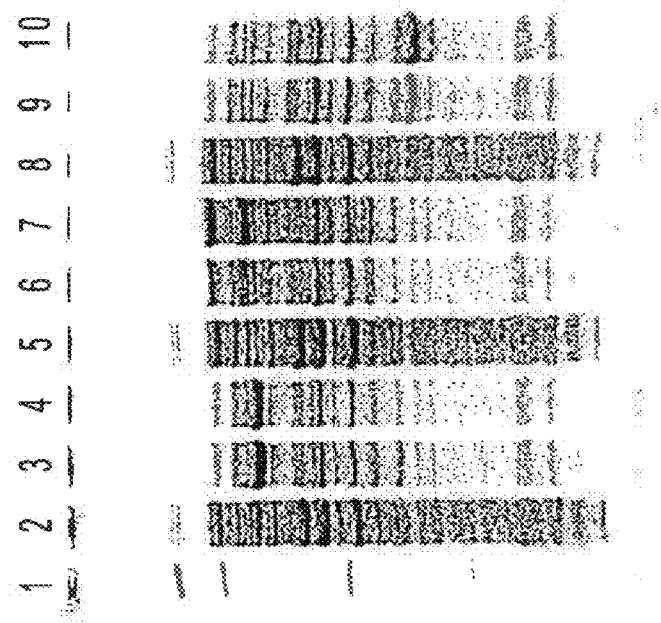
FIG. 5B shows the same gel after staining with a visible dye.
Figure 5A:
FIG. 5A shows the fluorescent detection of FlAsH-tagged proteins expressed in *E. coli* cells, with cell lysates treated with the compositions and according to the methods of the present invention and then resolved in a 4-12% NuPAGE gel run with MES running buffer.

Results are shown in FIGS. 5A (fluorescence detection) and 5B (visual detection after subsequent staining with SimplyBlue™ stain (Invitrogen Corp., Carlsbad, Calif.). Lanes were loaded as follows:
Lane 1: 3 μL BenchMark™ fluorescent standard
Lane 2: 10 μL GUS, uninduced
Lane 3: 10 μL GUS, 2 hour induction
Lane 4: 10 μL GUS, 4 hour induction
Lane 5: 10 μL human kinase, uninduced
Lane 6: 10 μL human kinase, 2 hour induction
Lane 7: 10 μL human kinase, 4 hour induction
Lane 8: 10 μL CAT, uninduced
Lane 9: 10 μL CAT, 2 hour induction
Lane 10: 10 μL CAT, 4 hour induction.

Results demonstrate excellent specificity of fluorescence labeling with very low nonspecific background fluorescence.

Example 2

Exemplary Results with Tagged Proteins Expressed In Vitro

Krev, Jun, CAT and E2F1 were expressed as tetracysteine-tagged fusions in vitro using the Expressway expression system (Invitrogen Corp., Carlsbad, Calif.), essentially according to manufacturer's instructions.

Samples were then treated for labeling of the tetracysteine tag essentially as in Example 1, above, and electrophoresed on a 4-12% NuPAGE® gel run with MES running buffer. Results are shown in FIGS. 6A (fluorescence detection) and 6B (visual detection after subsequent staining with SimplyBlue™ stain (Invitrogen Corp., Carlsbad, Calif.). Lanes were loaded as follows:
Lane 1: 5 μL BenchMark™ fluorescent standard
Lane 2: 10 μL control (no DNA)
Lane 3: 10 μL Krev expression
Lane 4: 10 μL Jun expression
Lane 5: 10 μL CAT expression
Lane 6: 10 μL E2F1 expression Results demonstrate excellent specificity of fluorescence labeling with very low nonspecific background fluorescence.

Example 3

Exemplary Results with Tagged Proteins Expressed in Mammalian Cells

Figure 7B:
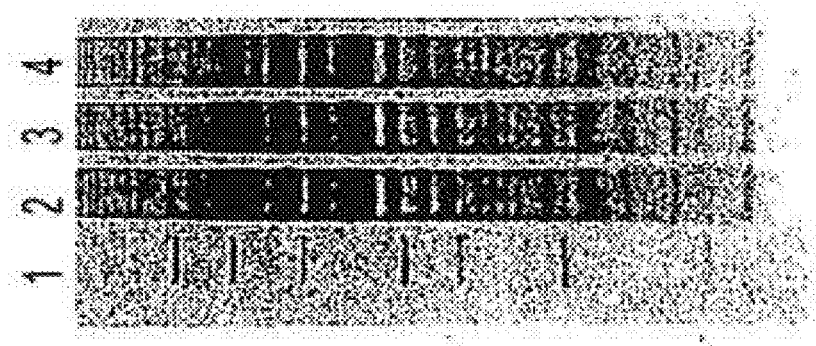
FIG. 7B shows the same gel after staining with a visible dye.
Figure 7A:
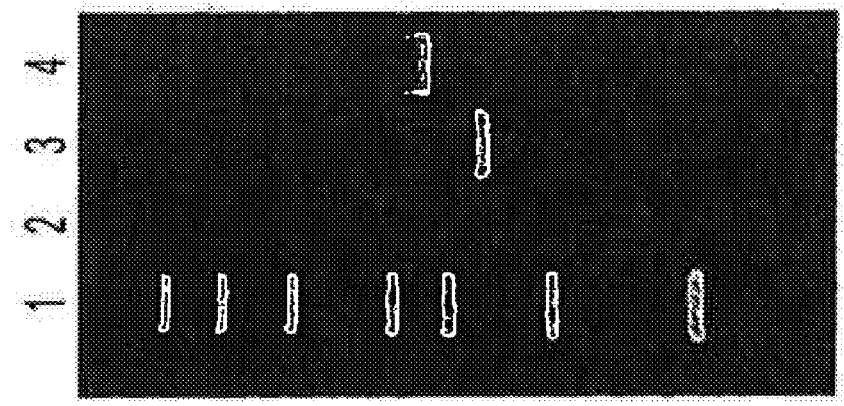
FIG. 7A shows the fluorescent detection of FlAsH-tagged proteins expressed in a human 293 cell line, with cell lysates treated with the compositions and according to the methods of the present invention and resolved in a 4-12% NuPAGE gel run with MES running buffer.
Figure 8B:
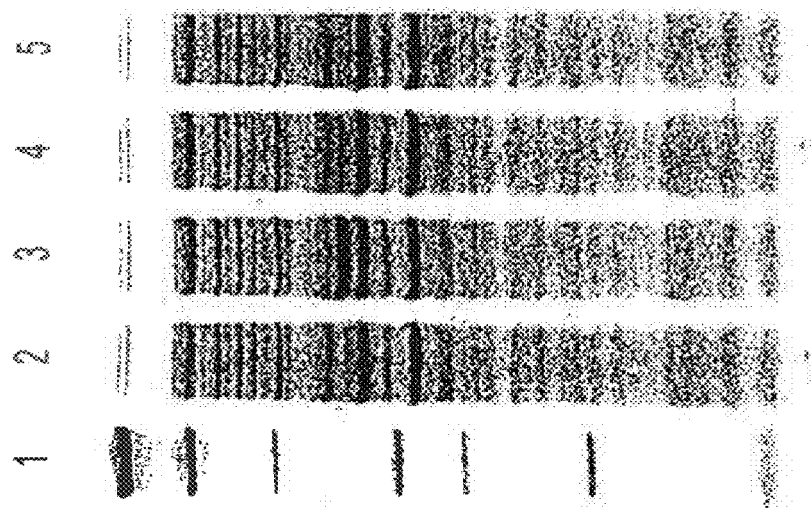
FIGS. 8A and 8B show the specificity of labeling of a 48 kDa tetracysteine-tagged fusion protein using the reductive competition and subsequent thiol blocking methods of the present invention, with panel A showing fluorescent detection, and panel B showing subsequent visual staining of the same NuPAGE® Novex 4-12% Bis-Tris gel, of which lane 1 was loaded with a spectrally matched fluorescent standard protein ladder, lane 2 loaded with a negative control *E. coli* extract, and lanes 3-5 respectively loaded with 1200 ng, 240 ng, and 48 ng of pure 48 kDa Lumio fusion protein mixed with *E. coli* lysate.
Figure 8A:
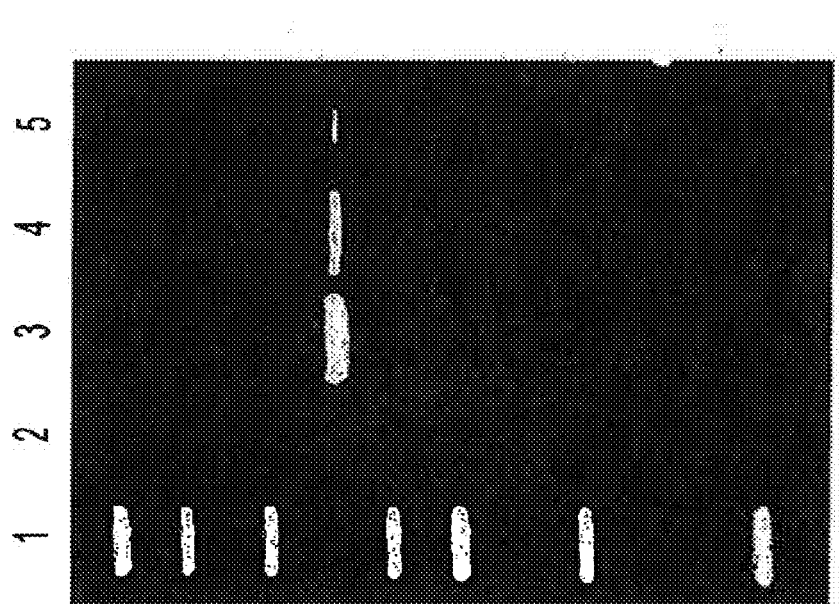

Orf6 and Orf7 tetracysteine-tagged proteins were expressed in GripTite™ cells, an engineered human 293 embryonic kidney cell line (Invitrogen Corp., Carlsbad, Calif.), according to manufacturer's instructions and standard protocols. Cell lysates were treated for labeling of the tetracysteine tag essentially as in Example 1, above, and electrophoresed on a 4-12% NuPAGE® gel run with MES running buffer. Results are shown in FIGS. 7A (fluorescence detection) and 7B (visual detection after subsequent staining with SimplyBlue™ stain (Invitrogen Corp., Carlsbad, Calif.). Lanes were loaded as follows:
Lane 1: 5 μL BenchMark™ fluorescent standard
Lane 2: 10 μL mock transfected control
Lane 3: 10 μL Orf6 lysate
Lane 4: 10 μL Orf7 lysate Results demonstrate excellent specificity of fluorescence labeling with very low nonspecific background fluorescence.

Example 4

Real-Time Monitoring of Tetracysteine-Tagged Protein Synthesis

Reducing agent, thiol competitor, and biarsenical fluorophore are added to the Expressway Plus™ Lumio™ cell-free in vitro transcription-translation extract (Invitrogen Corp., Carlsbad, Calif.). Protein production is observed in real-time by measuring directly from a microtiter plate using a 96 well plate reader. The excitation wavelength is set at 500 nm, while emission is monitored at 535 nm. Readings are taken at 10 minute intervals over a two hour incubation period, providing data analogous to those shown in FIG. 9.

All patents, patent publications, and published references cited herein are incorporated herein by reference in their entireties as if specifically and individually incorporated.

Although a number of embodiments and features are described herein, it will be understood by those skilled in the art that modification and variations of the described embodiments and features may be made without departing from either the spirit of the invention or the scope of the appended claims. All publications and patents cited herein are incorporated by reference in their entireties.

What is claimed is:

1. A method of labeling a tetracysteine-tagged protein species present in an inhomogeneous protein sample with a biarsenical fluorophore, the method comprising:
   a) treating the proteins in said sample in the presence of a composition comprising a thiol competitor and a biarsenical fluorophore, wherein each arsenic of the biarsenical fluorophore is bonded to a dithiol prior to said treating; and
   b) resolving the proteins in said sample by electrophoresis.

2. The method of claim 1, wherein said composition further comprises a reducing agent.

3. The method of claim 2, wherein said reducing agent is tributylphosphine (TBP).

4. The method of claim 2, wherein said reducing agent is at a concentration of at least about 10 μM.

5. The method of claim 4, wherein said reducing agent is at a concentration of at least about 1 mM.

6. The method of claim 5, wherein said reducing agent is at a concentration of at least about 10 mM.

7. The method of claim 6, wherein said reducing agent is at a concentration of at least about 100 mM.

8. The method of claim 2, wherein said biarsenical fluorophore is added to said sample after said thiol competitor and said reducing agent are added.

9. The method of claim 2, further comprising a step of:
   treating said sample with a thiol-blocking reagent after said treating of a) and before said resolving of b).

10. The method of claim 9, wherein said thiol-blocking reagent is selected from the group consisting of: alkylhalides, iodoacetamide, iodoacetic acid, dithiobis(2-nitrobenzoic acid) (DTNB), dithiobis(5-nitropyridine), maleimide and ethylenemaleimide.

11. The method of claim 10, wherein said thiol-blocking reagent is iodoacetamide.

12. The method of claim 10, wherein said thiol-blocking reagent is maleimide.

13. The method of claim 9, wherein said thiol competitor is a mono- or di-thiol, and said thiol-blocking reagent is present at a concentration insufficient to block all of said thiol competitor thiols.

14. The method of claim 13, wherein said thiol competitor is beta-mercaptoethanol (BME), said reducing agent is tributylphosphine (TBP), and said thiol-blocking agent is either iodoacetamide or maleimide.

15. The method of claim 9, wherein said electrophoresis is in a gel having substantially neutral pH.

16. The method of claim 15, wherein said gel is a Bis-Tris gel.

17. The method of claim 15, comprising a yet further step of detecting said tetracysteine-tagged protein among said resolved proteins in said gel.

18. The method of claim 17, wherein said detecting comprises exciting said fluorophore near its excitation maximum and observing fluorescence emission near its emission maximum.

19. The method of claim 18, wherein said gel is free of mechanical supports within which the gel was cast and within which the gel was electrophoresed.

20. The method of claim 1, wherein said thiol competitor is a monothiol.

21. The method of claim 20, wherein said monothiol is beta-mercaptoethanol (BME) and the BME is at a concentration greater than about 1 mM.

22. The method of claim 21, wherein said BME is at a concentration of at least about 5 mM.

23. The method of claim 22, wherein said BME is at a concentration of at least about 60 mM.

24. The method of claim 1, wherein said thiol competitor is a dithiol with concentration of at least 100 μM.

25. The method of claim 1, wherein said biarsenical fluorophore is a biarsenical derivative of fluorescein.

26. The method of claim 25, wherein said biarsenical fluorophore is 4'-5'-bis(1,3,2-dithioarsolan-2-yl)fluorescein-(2,2-ethanedithiol)2.

27. The method of claim 1, wherein said biarsenical fluorophore is a derivative of resorufin.

28. The method of claim 1, wherein said treating step is performed at temperatures above room temperature.

29. The method of claim 28, wherein said treating step is at a temperature of at least about 42° C.

30. The method of claim 29, wherein said treating step is at a temperature of at least about 50° C.

31. The method of claim 30, wherein said treating step is at a temperature of about 70° C.

32. The method of claim 1, wherein said treating of said proteins in the presence of a thiol competitor and biarsenical fluorophore is performed for a period of no more than about 2 hours.

33. The method of claim 32, wherein said treating is performed for a period of no more than about 1 hour.

34. The method of claim 33, wherein said treating is performed for a period of no more than about 30 minutes.

35. The method of claim 34, wherein said treating is for a period of no more than about 15 minutes.

36. The method of claim 35, wherein said treating is for a period of no more than about 10 minutes.

37. The method of claim 1, wherein,
said resolving is by gel electrophoresis.

38. The method of claim 37, comprising a yet further step of detecting said tetracysteine-tagged protein among said resolved proteins in said gel.

39. The method of claim 38, wherein said detecting comprises exciting said fluorophore near its excitation maximum and observing fluorescence emission near its emission maximum.

40. The method of claim 39, wherein said gel is free of mechanical supports within which the gel was cast and within which the gel was electrophoresed.

41. The method of claim 1, wherein said sample is a cell lysate.

* * * * *